US010286064B2

(12) United States Patent
Johnson et al.

(10) Patent No.: US 10,286,064 B2
(45) Date of Patent: May 14, 2019

(54) CATIONIC LIPID VACCINE COMPOSITIONS AND METHODS OF USE

(71) Applicants: PDS BIOTECHNOLOGY CORPORATION, Lawrenceburg, IN (US); THE UNITED STATES OF AMERICA AS REPRESENTED BY THE SEC. OF THE DEPT. OF HEALTH AND HUMAN SERVICE, Rockville, MD (US)

(72) Inventors: Kenya Johnson, Mason, OH (US); Eric Jacobson, Cincinnati, OH (US); Frank Bedu-Addo, Bethel, CT (US); Mikayel Mkrtichyan, Rockville, MD (US); Samir N. Khleif, Silver Spring, MD (US)

(73) Assignees: PDS Biotechnology Corporation, North Brunswick, NJ (US); THE UNITED STATES OF AMERICA AS REPRESENTED BY THE SEC. OF THE DEPT. OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 14/407,419

(22) PCT Filed: Jun. 13, 2013

(86) PCT No.: PCT/US2013/045578
§ 371 (c)(1),
(2) Date: Dec. 11, 2014

(87) PCT Pub. No.: WO2013/188627
PCT Pub. Date: Dec. 19, 2013

(65) Prior Publication Data
US 2015/0132340 A1  May 14, 2015

Related U.S. Application Data

(60) Provisional application No. 61/660,172, filed on Jun. 15, 2012.

(51) Int. Cl.
| *C07K 14/53* | (2006.01) |
| *A61K 39/39* | (2006.01) |
| *A61K 39/12* | (2006.01) |
| *A61K 39/00* | (2006.01) |

(52) U.S. Cl.
CPC .......... *A61K 39/39* (2013.01); *A61K 39/0005* (2013.01); *A61K 39/0011* (2013.01); *A61K 39/12* (2013.01); *A61K 2039/55511* (2013.01); *A61K 2039/55516* (2013.01); *A61K 2039/55522* (2013.01); *A61K 2039/55555* (2013.01); *A61K 2039/55566* (2013.01); *A61K 2039/585* (2013.01); *C12N 2710/20034* (2013.01)

(58) Field of Classification Search
None
See application file for complete search history.

(56) References Cited

U.S. PATENT DOCUMENTS

| 9,102,950 B2 | 8/2015 | Hartikka et al. | |
| 2007/0066552 A1* | 3/2007 | Clarke | A61K 8/606 514/44 R |
| 2008/0152665 A1* | 6/2008 | Leclerc | A61K 39/12 424/185.1 |
| 2010/0239657 A1 | 9/2010 | Kim et al. | |
| 2011/0110972 A1* | 5/2011 | Vasievich | A61K 31/685 424/196.11 |
| 2011/0305713 A1 | 12/2011 | Munn et al. | |
| 2012/0148622 A1 | 6/2012 | tenOever | |
| 2015/0132340 A1 | 5/2015 | Johnson et al. | |

FOREIGN PATENT DOCUMENTS

| RU | 2311911 C2 | | 12/2007 | |
| WO | WO93/22338 | * | 11/1993 | ............... C07K 7/06 |
| WO | WO2006/063382 | * | 6/2006 | ............. A61K 36/47 |
| WO | 2008148057 A2 | | 12/2008 | |
| WO | WO/2009/129227 | * | 10/2009 | ............ A61K 31/685 |
| WO | WO/2010/101663 | * | 9/2010 | ............. A61K 48/00 |

OTHER PUBLICATIONS

Dranoff G., GM-CSF based vaccines, Immunol. Rev. 188, 147-154, 2002.*
Supplementary European Search Report dated Jan. 22, 2016 from corresponding European Application No. 13804165.2.
Taiwanese Office Action dated Jun. 20, 2016, of corresponding Taiwanese Application No. 102121266, along with an English translation of the Search Report.
Sinha et al. (2007) Cross-Talk between Myeloid-Derived Suppressor Cells and Macrophages Subverts Tumor Immunity toward a Gabrilovich et al. (2009) Myeloid-derived-suppressor cells as regulators of the immune system, Nat. Rev. Immunol. 9(3):162-174 (pp. 1-26 NIH Manuscript).
Office Action for corresponding Russian Application No. 2015101110; dated Mar. 28, 2017, along with its English translation.
Office Action for corresponding Russian Application No. 2015101110; dated Aug. 8, 2017, along with its English translation.

* cited by examiner Type 2 Response, J. Immunol. 179:977-983.

Primary Examiner — Elly-Gerald Stoica
(74) Attorney, Agent, or Firm — DLA Piper LLP (US)

(57) ABSTRACT

The present disclosure provides vaccine compositions comprising at least one adjuvant and at least one therapeutic factor. The disclosure also provides methods of reducing an immune suppressor cell population in a mammal, methods of augmenting an immune response in a mammal, and methods of treating a disease in a mammal utilizing the vaccine compositions.

3 Claims, 4 Drawing Sheets
Specification includes a Sequence Listing.

SEQUENCE LISTING

```
<160> NUMBER OF SEQ ID NOS: 13

<210> SEQ ID NO 1
<211> LENGTH: 9
<212> TYPE: PRT
<213> ORGANISM: Homo sapiens

<400> SEQUENCE: 1

Arg Ala His Tyr Asn Ile Val Thr Phe
1               5

<210> SEQ ID NO 2
<211> LENGTH: 15
<212> TYPE: PRT
<213> ORGANISM: Homo sapiens

<400> SEQUENCE: 2

Gly Gln Ala Glu Pro Asp Arg Ala His Tyr Asn Ile Val Thr Phe
1               5                   10                  15
```

```
<210> SEQ ID NO 3
<211> LENGTH: 18
<212> TYPE: PRT
<213> ORGANISM: Artificial Sequence
<220> FEATURE:
<223> OTHER INFORMATION: Elongated peptide

<400> SEQUENCE: 3

Lys Ser Ser Gly Gln Ala Glu Pro Asp Arg Ala His Tyr Asn Ile Val
1               5                   10                  15

Thr Phe

<210> SEQ ID NO 4
<211> LENGTH: 10
<212> TYPE: PRT
<213> ORGANISM: Homo sapiens

<400> SEQUENCE: 4

Tyr Met Leu Asp Leu Gln Pro Glu Thr Thr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Elongated peptide

<400> SEQUENCE: 5

Lys Ser Ser Tyr Met Leu Asp Leu Gln Pro Glu Thr Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Elongated peptide

<400> SEQUENCE: 6

Met His Gly Asp Thr Pro Thr Leu His Glu Tyr Met Leu Asp Leu Gln
1               5                   10                  15

Pro Glu Thr Thr
            20

<210> SEQ ID NO 7
<211> LENGTH: 17
<212> TYPE: PRT
<213> ORGANISM: Artificial Sequence
<220> FEATURE:
<223> OTHER INFORMATION: Elongated peptide

<400> SEQUENCE: 7

Leu Leu Met Gly Thr Leu Gly Ile Val Cys Pro Ile Cys Ser Gln Lys
1               5                   10                  15

Pro

<210> SEQ ID NO 8
<211> LENGTH: 9
<212> TYPE: PRT
<213> ORGANISM: Artificial Sequence
<220> FEATURE:
<223> OTHER INFORMATION: Elongated peptide

<400> SEQUENCE: 8
```

```
Lys Val Pro Arg Asn Gln Asp Trp Leu
1               5
```

<210> SEQ ID NO 9
<211> LENGTH: 9
<212> TYPE: PRT
<213> ORGANISM: Homo sapiens

<400> SEQUENCE: 9

```
Ser Tyr Val Asp Phe Phe Val Trp Leu
1               5
```

<210> SEQ ID NO 10
<211> LENGTH: 9
<212> TYPE: PRT
<213> ORGANISM: Artificial Sequence
<220> FEATURE:
<223> OTHER INFORMATION: Elongated peptide

<400> SEQUENCE: 10

```
Lys Tyr Ile Cys Asn Ser Ser Cys Met
1               5
```

<210> SEQ ID NO 11
<211> LENGTH: 12
<212> TYPE: PRT
<213> ORGANISM: Artificial Sequence
<220> FEATURE:
<223> OTHER INFORMATION: Elongated peptide

<400> SEQUENCE: 11

```
Lys Ser Ser Lys Val Pro Arg Asn Gln Asp Trp Leu
1               5                   10
```

<210> SEQ ID NO 12
<211> LENGTH: 23
<212> TYPE: PRT
<213> ORGANISM: Artificial Sequence
<220> FEATURE:
<223> OTHER INFORMATION: Elongated peptide

<400> SEQUENCE: 12

```
Lys Ser Ser Met His Gly Asp Thr Pro Thr Leu His Glu Tyr Met Leu
1               5                   10                  15

Asp Leu Gln Pro Glu Thr Thr
            20
```

<210> SEQ ID NO 13
<211> LENGTH: 20
<212> TYPE: PRT
<213> ORGANISM: Artificial Sequence
<220> FEATURE:
<223> OTHER INFORMATION: Elongated peptide

<400> SEQUENCE: 13

```
Lys Ser Ser Leu Leu Met Gly Thr Leu Gly Ile Val Cys Pro Ile Cys
1               5                   10                  15

Ser Gln Lys Pro
            20
```

CATIONIC LIPID VACCINE COMPOSITIONS AND METHODS OF USE

CROSS-REFERENCE TO RELATED APPLICATIONS

This application is a national stage entry under 35 USC § 371(b) of PCT International Application No. PCT/US2013/045578, filed Jun. 13, 2013, which claims the benefit under 35 USC § 119(e) of U.S. Provisional Application Ser. No. 61/660,172, filed on Jun. 15, 2012, the entire disclosures of which are incorporated herein by reference.

GOVERNMENT RIGHTS

Part of the work leading to this invention was carried out with the United States Government support provided under the National Institutes of Health CRADA No. 2644. Therefore, the United States Government has certain rights in and to the present invention.

INCORPORATION BY REFERENCE OF MATERIAL SUBMITTED ELECTRONICALLY

Incorporated by reference in its entirety is a computer-readable sequence listing submitted concurrently herewith and identified as follows: one 3,228 byte ASCII (text) file named "225611_ST25.txt", created on Jun. 12, 2013.

TECHNICAL FIELD

Development of safe and effective immunotherapies and therapeutic vaccines for human use remains an important medical need for patients worldwide. Typically, a vaccine composition includes an antigen to stimulate a targeted immune response. However, some developmental vaccines are ineffective because they are weak stimulators of an immune response in a broad mammalian population. For example, the antigen in the vaccine composition may be poorly immunogenic in the mammal. In addition, some vaccines may not efficiently deliver antigens to the antigen presenting cells ("APCs") of the mammal's immune system.

Myeloid-derived suppressor cells (MDSCs) are a heterogeneous population of early myeloid progenitors which have the capacity to suppress the adaptive immune response in patients, such as response mediated by $CD4^+$ and $CD8^+$ T cells. MDSCs are known to secrete immunosuppressive cytokines and induce regulatory T cell development. Furthermore, MDSCs are induced by pro-inflammatory cytokines and are found in increased numbers in infectious and in inflammatory pathological conditions.

MDSCs accumulate in the blood, bone marrow, and secondary lymphoid organs of tumor-bearing mice and their presence in the tumor microenvironment has been suggested to have a causative role in promoting tumor-associated immune suppression. Importantly, tumor antigen-specific T-cell tolerance has been reported to be a critical element of tumor escape. Furthermore, MDSCs have been found to be present in most cancer patients. Significant research is currently being conducted within the industry to identify a means of inhibiting immune suppressive cells, for example MDSCs and T-regulatory cells, as a means of improving the T-cell responses to attack and kill the infected cells. Current practice in the industry focuses on exploring the use of blocking antibodies to block and inhibit relevant immune suppressive factors. A vaccine such as the human antibody Ipilimumab may be used to block cytotoxic T-lymphocyte associated antigen-4 (CTLA-4), known to play a role in regulating immune responses as a therapeutic vaccine to treat melanoma.

BACKGROUND AND SUMMARY OF THE INVENTION

Vaccines also typically include adjuvants in an attempt to enhance the efficacy of antigens in the vaccine composition. For example, adjuvants such as water-in-oil emulsions, alum (e.g., aluminum salts), and other chemicals are typically utilized to enhance antigen response in a mammal. In addition to traditional adjuvants, other adjuvants with intrinsic immune effects (e.g., influenza virosomes and Chiron's MF59) may be used. However, these adjuvants are also undesirable because evidence from animal models (according to clinical trial reports on HSV and influenza vaccines) suggests that they merely enhance production of neutralizing antibodies rather than enhancing T-cell responses in animals.

Therefore, there exists a need for new vaccine compositions that effectively deliver antigens or promote antigen uptake by the antigen presenting cells in order to stimulate an immune response in a mammal, as well inhibiting immune suppressive cells to improve the immune response in a mammal. Moreover, new and effective methods of stimulating cell mediated immune responses in mammals, possibly by including a safe and effective immunologic modifier ("immunomodulator") in a vaccine composition along with a therapeutic factor, are also very desirable. Accordingly, the present disclosure provides vaccine compositions and method of using the compositions that exhibit desirable properties and provide related advantages for improvement in reducing an immune suppressor cell population and augmenting an immune response in a mammal.

The present disclosure provides vaccine compositions comprising at least one adjuvant and at least one therapeutic factor. The disclosure also provides methods of reducing an immune suppressor cell population in a mammal, methods of augmenting an immune response in a mammal, and methods of treating a disease in a mammal utilizing the vaccine compositions.

The vaccine compositions and methods according to the present disclosure provide several advantages compared to other compositions and methods in the art. First, the vaccine compositions include an adjuvant that is an immunomodulator to enhance, direct, or promote an appropriate immune response in a mammal. Immunomodulators have the potential to effectively boost a mammal's immune response to antigens if they are included in a vaccine composition. For example, an immunomodulator may advantageously accomplish one or more of the following: (1) improve antigen delivery and/or processing in the APC, (2) induce the production of immunomodulatory cytokines that favor the development of immune responses to the antigen, thus promoting cell mediated immunity, including cytotoxic T-lymphocytes ("CTL"), (3) reduce the number of immunizations or the amount of antigen required for an effective vaccine, (4) increase the biological or immunological half-life of the vaccine antigen, and (5) overcome immune tolerance to antigen by inhibiting immune suppressive factors. In some embodiments, cationic lipid-based adjuvants may be utilized potent immunomodifying adjuvants and can elicit superior T-cell and antibody immune responses in vaccine compositions.

Second, the vaccine compositions in the current disclosure include a therapeutic factor such as a cytokine that as a combination can reduce an immune suppressor cell population in a mammal, which can improve the immune response of a mammal in response to disease. Current research to identify means to inhibit immune suppressive cells such as MDSC and T-regulatory cells utilize complex blocking antibodies. Consequently, administration of a potent vaccine composition including a therapeutic factor such as a cytokine can be easier to administer to a patient and improve immune response, particularly in tumors.

Third, the vaccine compositions in the current disclosure including a therapeutic factor can cause a reduction in MDSC both with and without a disease-specific antigen, thus resulting in a unique and powerful approach to treating diseases such as cancer by facilitating the natural activation of antigen-specific T-cells while simultaneously reducing the immune suppressor cell population. The vaccine compositions including a therapeutic factor result in the generation of superior disease-specific immune responses, which are not observed when either the adjuvant or the therapeutic factor alone is formulated with the antigen.

Finally, the therapeutic factor, when combined with cationic lipid adjuvant to form the vaccine composition, results in a unique synergistic improvement in immune response in a mammal. Combinations of therapeutic factor (e.g., GM-CSF) with other adjuvants (e.g., incomplete Freund's adjuvant (IFA) or anti-CD40+ IFA) do not result in similar synergistic improvement in immune response. Therefore, the combination of the cationic lipid adjuvant and the therapeutic factor specifically and significantly result in a synergistic improvement in immune response that cannot be replicated using other commonly used adjuvants.

The following numbered embodiments are contemplated and are non-limiting:

1. A vaccine composition comprising an adjuvant and a therapeutic factor.
2. The vaccine composition of clause 1, wherein the adjuvant is an immunomodulator.
3. The vaccine composition of clause 1 or clause 2, wherein the adjuvant is a cationic lipid.
4. The vaccine composition of clause 3, wherein the cationic lipid is purified.
5. The vaccine composition of clause 3 or clause 4, wherein the cationic lipid is selected from the group consisting of DOTAP, DOTMA, DOEPC, and combinations thereof.
6. The vaccine composition of any one of clauses 3 to 5, wherein the cationic lipid is DOTAP.
7. The vaccine composition of any one of clauses 3 to 5, wherein the cationic lipid is DOTMA.
8. The vaccine composition of any one of clauses 3 to 5, wherein the cationic lipid is DOEPC.
9. The vaccine composition of clause 1 or clause 2, wherein the adjuvant is an enantiomer of a cationic lipid.
10. The vaccine composition of clause 9, wherein the enantiomer is purified.
11. The vaccine composition of clause 9 or clause 10, wherein the enantiomer is R-DOTAP or S-DOTAP.
12. The vaccine composition of clause 9 or clause 10, wherein the enantiomer is R-DOTAP.
13. The vaccine composition of clause 9 or clause 10, wherein the enantiomer is S-DOTAP.
14. The vaccine composition of clause 9 or clause 10, wherein the enantiomer is R-DOTMA or S-DOTMA.
15. The vaccine composition of clause 9 or clause 10, wherein the enantiomer is R-DOTMA.
16. The vaccine composition of clause 9 or clause 10, wherein the enantiomer is S-DOTMA.
17. The vaccine composition of clause 9 or clause 10, wherein the enantiomer is R-DOEPC or S-DOEPC.
18. The vaccine composition of clause 9 or clause 10, wherein the enantiomer is R-DOEPC.
19. The vaccine composition of clause 9 or clause 10, wherein the enantiomer is S-DOEPC.
20. The vaccine composition of any one of clauses 1 to 19, wherein the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, IFN-α, IFN-β, soluble CD23, LIF, and combinations thereof.
21. The vaccine composition of any one of clauses 1 to 19, wherein the therapeutic factor is a cytokine.
22. The vaccine composition of clause 20, wherein the cytokine is GM-CSF.
23. The vaccine composition of any one of clauses 1 to 19, wherein the therapeutic factor is an immune cell growth factor.
24. The vaccine composition of any one of clauses 1 to 23, wherein the composition further comprises one or more antigens.
25. The vaccine composition of clause 24, wherein one or more antigens is a protein-based antigen.
26. The vaccine composition of clause 24, wherein one or more antigens is a peptide-based antigen.
27. The vaccine composition of any one of clauses 24 to 26, wherein one or more antigens is selected from the group consisting of a cancer antigen, a viral antigen, a bacterial antigen, and a pathogenic antigen.
28. The vaccine composition of any one of clauses 24 to 26, wherein one or more antigens is a cancer antigen.
29. The vaccine composition of any one of clauses 24 to 26, wherein one or more antigens is a viral antigen.
30. The vaccine composition of any one of clauses 24 to 26, wherein one or more antigens is a bacterial antigen.
31. The vaccine composition of any one of clauses 24 to 26, wherein one or more antigens is a pathogenic antigen.
32. The vaccine composition of clause 31, wherein the pathogenic antigen is a synthetic or recombinant antigen.
33. The vaccine composition of any one of clauses 24 to 32, wherein at least one antigen is an HPV protein or peptide.
34. The vaccine composition of any one of clauses 24 to 33, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).
35. The vaccine composition of any one of clauses 24 to 33, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.
36. The vaccine composition of any one of clauses 24 to 33, wherein the antiigens comprise one or more of the gp100 sequence (KVPRNQDWL [SEQ. ID. No. 8]) and the TRP2 sequence (SYVDFFVWL [SEQ. ID. No. 9]).

37. The vaccine composition of any one of clauses 24 to 33, wherein the antigen comprises the sequence RAHYNIVTF (SEQ. ID. NO: 1).

38. The vaccine composition of any one of clauses 24 to 33, wherein the antigen comprises the sequence GQAEP-DRAHYNIVTF (SEQ. ID. NO: 2).

39. The vaccine composition of any one of clauses 24 to 33, wherein the antigen comprises the sequence KSSGQAE-PDRAHYNIVTF (SEQ. ID. NO: 3).

40. The vaccine composition of any one of clauses 24 to 33, wherein the antigen comprises the sequence YMLDLQ-PETT (SEQ. ID. NO: 4).

41. The vaccine composition of any one of clauses 24 to 33, wherein the antigen comprises the sequence KSSYMLDLQPETT (SEQ. ID. NO: 5).

42. The vaccine composition of any one of clauses 24 to 33, wherein the antigen comprises the sequence MHGDTPTLHEYMLDLQPETT (SEQ. ID. NO: 6).

43. The vaccine composition of any one of clauses 24 to 33, wherein the antigen comprises the sequence LLMGTL-GIVCPICSQKP (SEQ. ID. NO: 7).

44. The vaccine composition of any one of clauses 24 to 33, wherein the antigen comprises the sequence KVPRN-QDWL (SEQ. ID. NO: 8).

45. The vaccine composition of any one of clauses 24 to 33, wherein the antigen comprises the sequence SYVD-FFVWL (SEQ. ID. NO: 9).

46. The vaccine composition of any one of clauses 24 to 33, wherein the antigen comprises the sequence KYICNS-SCM (SEQ. ID. NO: 10).

47. The vaccine composition of any one of clauses 24 to 33, wherein the antigen comprises the sequence KSSK-VPRNQDWL (SEQ. ID. NO: 11).

48. The vaccine composition of any one of clauses 24 to 47, wherein at least one antigen is selected from the group consisting of a lipoprotein, a lipopeptide, and a protein or peptide modified with an amino acid sequence having an increased hydrophobicity or a decreased hydrophobicity.

49. The vaccine composition of any one of clauses 24 to 48, wherein one or more antigens is a lipidated antigen or an antigen modified to increase hydrophobicity of the antigen.

50. The vaccine composition of any one of clauses 24 to 49, wherein at least one antigen is a modified protein or peptide.

51. The vaccine composition of clause 50, wherein the modified protein or peptide is bonded to a hydrophobic group.

52. The vaccine composition of clause 51, wherein the modified protein or peptide bonded to a hydrophobic group further comprises a linker sequence between the antigen and the hydrophobic group.

53. The vaccine composition of clause 51 or 52, wherein the hydrophobic group is a palmitoyl group.

54. The vaccine composition of any one of clauses 24 to 53, wherein at least one antigen is an unmodified protein or peptide.

55. The vaccine composition of any one of clauses 1 to 54, wherein the vaccine composition induces an immune response in a mammal by activating the mitogen-activated protein (MAP) kinase signaling pathway.

56. The vaccine composition of clause 55, wherein the MAP kinase signaling pathway is activated by stimulating at least one of extracellular signal-regulated kinase ("ERK")-1, ERK-2, and p38.

57. The vaccine composition of any one of clauses 1 to 56, wherein the vaccine composition enhances functional antigen-specific CD8+ T lymphocyte response in a mammal.

58. The vaccine composition of clause 57, wherein the mammal is a human.

59. A method of reducing an immune suppressor cell population in a mammal, said method comprising the step of administering an effective amount of a vaccine composition to the mammal, wherein the vaccine composition comprises an adjuvant and a therapeutic factor.

60. The method of clause 59, wherein the immune suppressor cell is MDSC.

61. The method of clause 59, wherein the immune suppressor cell is a T regulatory cell.

62. The method of any one of clauses 59 to 61, wherein the reduction results in an increase in T-cell response in the mammal.

63. The method of clause 62, wherein the T-cell is a tumor-infiltrated T-cell.

64. The method of clause 62 or clause 63, wherein the T-cell response is a CD4+ T-cell response.

65. The method of clause 64, wherein the CD4+ T-cell is a tumor-infiltrated CD4+ T-cell.

66. The method of clause 62 or clause 63, wherein the T-cell response is a CD8+ T-cell response.

67. The method of clause 66, wherein the CD8+ T-cell is a tumor-infiltrated CD8+ T-cell.

68. The method of any one of clauses 59 to 67, wherein the mammal is a human.

69. The method of any one of clauses 59 to 68, wherein the adjuvant is an immunomodulator.

70. The method of any one of clauses 59 to 69, wherein the adjuvant is a cationic lipid.

71. The method of clause 70, wherein the cationic lipid is purified.

72. The method of clause 70 or clause 71, wherein the cationic lipid is selected from the group consisting of DOTAP, DOTMA, DOEPC, and combinations thereof.

73. The method of any one of clauses 70 to 72, wherein the cationic lipid is DOTAP.

74. The method of any one of clauses 70 to 72, wherein the cationic lipid is DOTMA.

75. The method of any one of clauses 70 to 72, wherein the cationic lipid is DOEPC.

76. The method of any one of clauses 59 to 69, wherein the adjuvant is an enantiomer of a cationic lipid.

77. The method of clause 76, wherein the enantiomer is purified.

78. The method of clause 76 or clause 77, wherein the enantiomer is R-DOTAP or S-DOTAP.

79. The method of clause 76 or clause 77, wherein the enantiomer is R-DOTAP.

80. The method of clause 76 or clause 77, wherein the enantiomer is S-DOTAP.

81. The method of clause 76 or clause 77, wherein the enantiomer is R-DOTMA or S-DOTMA.

82. The method of clause 76 or clause 77, wherein the enantiomer is R-DOTMA.

83. The method of clause 76 or clause 77, wherein the enantiomer is S-DOTMA.

84. The method of clause 76 or clause 77, wherein the enantiomer is R-DOEPC or S-DOEPC.

85. The method of clause 76 or clause 77, wherein the enantiomer is R-DOEPC.

86. The method of clause 76 or clause 77, wherein the enantiomer is S-DOEPC.

87. The method of any one of clauses 59 to 86, wherein the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, IFN-α, IFN-β, soluble CD23, LIF, and combinations thereof.

88. The method of any one of clauses 59 to 86, wherein the therapeutic factor is a cytokine.

89. The method of clause 88, wherein the cytokine is GM-CSF.

90. The method of any one of clauses 59 to 86, wherein the therapeutic factor is an immune cell growth factor.

91. The method of any one of clauses 59 to 90, wherein the composition further comprises one or more antigens.

92. The method of clause 91, wherein one or more antigens is a protein-based antigen.

93. The method of clause 91, wherein one or more antigens is a peptide-based antigen.

94. The method of any one of clauses 91 to 93, wherein one or more antigens is selected from the group consisting of a cancer antigen, a viral antigen, a bacterial antigen, and a pathogenic antigen.

95. The method of any one of clauses 91 to 93, wherein one or more antigens is a cancer antigen.

96. The method of any one of clauses 91 to 93, wherein one or more antigens is a viral antigen.

97. The method of any one of clauses 91 to 93, wherein one or more antigens is a bacterial antigen.

98. The method of any one of clauses 91 to 93, wherein one or more antigens is a pathogenic antigen.

99. The method of clause 98, wherein the pathogenic antigen is a synthetic or recombinant antigen.

100. The method of any one of clauses 91 to 99, wherein at least one antigen is an HPV protein or peptide.

101. The method of any one of clauses 91 to 100, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).

102. The method of any one of clauses 91 to 100, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

103. The method of any one of clauses 91 to 100, wherein the antigens comprise one or more of the gp100 sequence (KVPRNQDWL [SEQ. ID. No. 8]) and the TRP2 sequence (SYVDFFVWL [SEQ. ID. No. 9]).

104. The method of any one of clauses 91 to 100, wherein the antigen comprises the sequence RAHYNIVTF (SEQ. ID. NO: 1).

105. The method of any one of clauses 91 to 100, wherein the antigen comprises the sequence GQAEPDRAHYNIVTF (SEQ. ID. NO: 2).

106. The method of any one of clauses 91 to 100, wherein the antigen comprises the sequence KSSGQAEPDRAHYNIVTF (SEQ. ID. NO: 3).

107. The method of any one of clauses 91 to 100, wherein the antigen comprises the sequence YMLDLQPETT (SEQ. ID. NO: 4).

108. The method of any one of clauses 91 to 100, wherein the antigen comprises the sequence KSSYMLDLQPETT (SEQ. ID. NO: 5).

109. The method of any one of clauses 91 to 100, wherein the antigen comprises the sequence MHGDTPTLHEYMLDLQPETT (SEQ. ID. NO: 6).

110. The method of any one of clauses 91 to 100, wherein the antigen comprises the sequence LLMGTLGIVCPICSQKP (SEQ. ID. NO: 7).

111. The method of any one of clauses 91 to 100, wherein the antigen comprises the sequence KVPRNQDWL (SEQ. ID. NO: 8).

112. The method of any one of clauses 91 to 100, wherein the antigen comprises the sequence SYVDFFVWL (SEQ. ID. NO: 9).

113. The method of any one of clauses 91 to 100, wherein the antigen comprises the sequence KYICNSSCM (SEQ. ID. NO: 10).

114. The method of any one of clauses 91 to 100, wherein the antigen comprises the sequence KSSKVPRNQDWL (SEQ. ID. NO: 11).

115. The method of any one of clauses 91 to 114, wherein at least one antigen is selected from the group consisting of a lipoprotein, a lipopeptide, and a protein or peptide modified with an amino acid sequence having an increased hydrophobicity or a decreased hydrophobicity.

116. The method of any one of clauses 91 to 115, wherein one or more antigens is a lipidated antigen or an antigen modified to increase hydrophobicity of the antigen.

117. The method of any one of clauses 91 to 116, wherein at least one antigen is a modified protein or peptide.

118. The method of clause 117, wherein the modified protein or peptide is bonded to a hydrophobic group.

119. The method of clause 118, wherein the modified protein or peptide bonded to a hydrophobic group further comprises a linker sequence between the antigen and the hydrophobic group.

120. The method of clause 118 or 119, wherein the hydrophobic group is a palmitoyl group.

121. The method of any one of clauses 91 to 120, wherein at least one antigen is an unmodified protein or peptide.

122. The method of any one of clauses 59 to 121, wherein the administration activates an immune response via the MAP kinase signaling pathway in cells of the immune system of the mammal.

123. The method of clause 122, wherein the MAP kinase signaling pathway is activated by stimulating at least one of ERK-1, ERK-2, and p38.

124. The method of clause 122 or clause 123, wherein the immune response activates cytotoxic T lymphocytes in the mammal.

125. The method of clause 124, wherein the cytotoxic T lymphocytes are CD8+ T cells.

126. The method of any one of clauses 122 to 125, wherein the immune response activates an antibody response in the mammal.

127. The method of any one of clauses 122 to 126, wherein the immune response activates interferon-gamma (IFN-γ) in the mammal.

128. The method of any one of clauses 59 to 127, wherein the administration enhances functional antigen-specific CD8+ T lymphocyte response.

129. A method of augmenting an immune response in a mammal, said method comprising the step of administering an effective amount of a vaccine composition to the mammal, wherein the vaccine composition comprises an adjuvant and a therapeutic factor.

130. The method of clause 129, wherein the reduction results in an increase in T-cell response in the mammal.

131. The method of clause 130, wherein the T-cell is a tumor-infiltrated T-cell.

132. The method of clause 130 or clause 131, wherein the T-cell response is a CD4+ T-cell response.

133. The method of clause 132, wherein the CD4+ T-cell is a tumor-infiltrated CD4+ T-cell.

134. The method of any one of clauses 129 to 133, wherein the T-cell response is a CD8+ T-cell response.

135. The method of clause 134, wherein the CD8+ T-cell is a tumor-infiltrated CD8+ T-cell.

136. The method of any one of clauses 129 to 135, wherein the mammal is a human.

137. The method of any one of clauses 129 to 136, wherein the adjuvant is an immunomodulator.

138. The method of any one of clauses 129 to 137, wherein the adjuvant is a cationic lipid.

139. The method of clause 138, wherein the cationic lipid is purified.

140. The method of clause 138 or clause 139, wherein the cationic lipid is selected from the group consisting of DOTAP, DOTMA, DOEPC, and combinations thereof.

141. The method of any one of clauses 138 to 140, wherein the cationic lipid is DOTAP.

142. The method of any one of clauses 138 to 140, wherein the cationic lipid is DOTMA.

143. The method of any one of clauses 138 to 140, wherein the cationic lipid is DOEPC.

144. The method of any one of clauses 129 to 137, wherein the adjuvant is an enantiomer of a cationic lipid.

145. The method of clause 144, wherein the enantiomer is purified.

146. The method of clause 144 or clause 145, wherein the enantiomer is R-DOTAP or S-DOTAP.

147. The method of clause 144 or clause 145, wherein the enantiomer is R-DOTAP.

148. The method of clause 144 or clause 145, wherein the enantiomer is S-DOTAP.

149. The method of clause 144 or clause 145, wherein the enantiomer is R-DOTMA or S-DOTMA.

150. The method of clause 144 or clause 145, wherein the enantiomer is R-DOTMA.

151. The method of clause 144 or clause 145, wherein the enantiomer is S-DOTMA.

152. The method of clause 144 or clause 145, wherein the enantiomer is R-DOEPC or S-DOEPC.

153. The method of clause 144 or clause 145, wherein the enantiomer is R-DOEPC.

154. The method of clause 144 or clause 145, wherein the enantiomer is S-DOEPC. 155. The method of any one of clauses 129 to 154, wherein the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, IFN-α, IFN-β, soluble CD23, LIF, and combinations thereof.

156. The method of any one of clauses 129 to 154, wherein the therapeutic factor is a cytokine.

157. The method of clause 156, wherein the cytokine is GM-CSF.

158. The method of any one of clauses 129 to 154, wherein the therapeutic factor is an immune cell growth factor.

159. The method of any one of clauses 129 to 158, wherein the composition further comprises one or more antigens.

160. The method of clause 159, wherein one or more antigens is a protein-based antigen.

161. The method of clause 159, wherein one or more antigens is a peptide-based antigen.

162. The method of any one of clauses 159 to 161, wherein one or more antigens is selected from the group consisting of a cancer antigen, a viral antigen, a bacterial antigen, and a pathogenic antigen.

163. The method of any one of clauses 159 to 161, wherein one or more antigens is a cancer antigen.

164. The method of any one of clauses 159 to 161, wherein one or more antigens is a viral antigen.

165. The method of any one of clauses 159 to 161, wherein one or more antigens is a bacterial antigen.

166. The method of any one of clauses 159 to 161, wherein one or more antigens is a pathogenic antigen.

167. The method of clause 166, wherein the pathogenic antigen is a synthetic or recombinant antigen.

168. The method of any one of clauses 159 to 167, wherein at least one antigen is an HPV protein or peptide.

169. The method of any one of clauses 159 to 168, wherein at least one antigen comprises a sequence selected from the group consisting of RAHYNIVTF (SEQ. ID. NO: 1), GQAEPDRAHYNIVTF (SEQ. ID. NO: 2), KSSGQAE-PDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRN-QDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).

170. The method of any one of clauses 159 to 168, wherein at least one antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

171. The method of any one of clauses 159 to 168, wherein the antigens comprise one or more of the gp100 sequence (KVPRNQDWL [SEQ. ID. No. 8]) and the TRP2 sequence (SYVDFFVWL [SEQ. ID. No. 9]).

172. The method of any one of clauses 159 to 168, wherein the antigen comprises the sequence RAHYNIVTF (SEQ. ID. NO: 1).

173. The method of any one of clauses 159 to 168, wherein the antigen comprises the sequence GQAEP-DRAHYNIVTF (SEQ. ID. NO: 2).

174. The method of any one of clauses 159 to 168, wherein the antigen comprises the sequence KSSGQAEP-DRAHYNIVTF (SEQ. ID. NO: 3).

175. The method of any one of clauses 159 to 168, wherein the antigen comprises the sequence YMLDLQ-PETT (SEQ. ID. NO: 4).

176. The method of any one of clauses 159 to 168, wherein the antigen comprises the sequence KSSYMLD-LQPETT (SEQ. ID. NO: 5).

177. The method of any one of clauses 159 to 168, wherein the antigen comprises the sequence MHGDTPTL-HEYMLDLQPETT (SEQ. ID. NO: 6).

178. The method of any one of clauses 159 to 168, wherein the antigen comprises the sequence LLMGTL-GIVCPICSQKP (SEQ. ID. NO: 7).

179. The method of any one of clauses 159 to 168, wherein the antigen comprises the sequence KVPRNQDWL (SEQ. ID. NO: 8).

180. The method of any one of clauses 159 to 168, wherein the antigen comprises the sequence SYVDFFVWL (SEQ. ID. NO: 9).

181. The method of any one of clauses 159 to 168, wherein the antigen comprises the sequence KYICNSSCM (SEQ. ID. NO: 10).

182. The method of any one of clauses 159 to 168, wherein the antigen comprises the sequence KSSKVPRNQDWL (SEQ. ID. NO: 11).

183. The method of any one of clauses 159 to 182, wherein at least one antigen is selected from the group consisting of a lipoprotein, a lipopeptide, and a protein or peptide modified with an amino acid sequence having an increased hydrophobicity or a decreased hydrophobicity.

184. The method of any one of clauses 159 to 183, wherein one or more antigens is a lipidated antigen or an antigen modified to increase hydrophobicity of the antigen.

185. The method of any one of clauses 159 to 184, wherein at least one antigen is a modified protein or peptide.

186. The method of clause 185, wherein the modified protein or peptide is bonded to a hydrophobic group.

187. The method of clause 185, wherein the modified protein or peptide bonded to a hydrophobic group further comprises a linker sequence between the antigen and the hydrophobic group.

188. The method of clause 186 or 187, wherein the hydrophobic group is a palmitoyl group.

189. The method of any one of clauses 159 to 188, wherein at least one antigen is an unmodified protein or peptide.

190. The method of any one of clauses 129 to 189, wherein the administration activates an immune response via the MAP kinase signaling pathway in cells of the immune system of the mammal.

191. The method of clause 190, wherein the MAP kinase signaling pathway is activated by stimulating at least one of ERK-1, ERK-2, and p38.

192. The method of clause 190 or clause 191, wherein the immune response activates cytotoxic T lymphocytes in the mammal.

193. The method of clause 192, wherein the cytotoxic T lymphocytes are CD8+ T cells.

194. The method of any one of clauses 190 to 193, wherein the immune response activates an antibody response in the mammal.

195. The method of any one of clauses 190 to 194, wherein the immune response activates interferon-gamma (IFN-γ) in the mammal.

196. The method of any one of clauses 129 to 195, wherein the administration enhances functional antigen-specific CD8+ T lymphocyte response.

197. A method of treating a disease in a mammal, said method comprising the step of administering an effective amount of a vaccine composition to the mammal, wherein the vaccine composition comprises an adjuvant and a therapeutic factor.

198. The method of clause 197, wherein the method is a prophylactic treatment.

199. The method of clause 197 or clause 198, wherein the disease is a cancer.

200. The method of any one of clauses 197 to 199, wherein the adjuvant is an immunomodulator.

201. The method of any one of clauses 197 to 200, wherein the adjuvant is a cationic lipid.

202. The method of clause 201, wherein the cationic lipid is purified.

203. The method of clause 201 or clause 202, wherein the cationic lipid is selected from the group consisting of DOTAP, DOTMA, DOEPC, and combinations thereof.

204. The method of any one of clauses 201 to 203, wherein the cationic lipid is DOTAP.

205. The method of any one of clauses 201 to 203, wherein the cationic lipid is DOTMA.

206. The method of any one of clauses 201 to 203, wherein the cationic lipid is DOEPC.

207. The method of any one of clauses 197 to 200, wherein the adjuvant is an enantiomer of a cationic lipid.

208. The method of clause 207, wherein the enantiomer is purified.

209. The method of clause 207 or clause 208, wherein the enantiomer is R-DOTAP or S-DOTAP.

210. The method of clause 207 or clause 208, wherein the enantiomer is R-DOTAP.

211. The method of clause 207 or clause 208, wherein the enantiomer is S-DOTAP.

212. The method of clause 207 or clause 208, wherein the enantiomer is R-DOTMA or S-DOTMA.

213. The method of clause 207 or clause 208, wherein the enantiomer is R-DOTMA.

214. The method of clause 207 or clause 208, wherein the enantiomer is S-DOTMA.

215. The method of clause 207 or clause 208, wherein the enantiomer is R-DOEPC or S-DOEPC.

216. The method of clause 207 or clause 208, wherein the enantiomer is R-DOEPC.

217. The method of clause 207 or clause 208, wherein the enantiomer is S-DOEPC.

218. The method of any one of clauses 197 to 217, wherein the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, IFN-α, IFN-β, soluble CD23, LIF, and combinations thereof.

219. The method of any one of clauses 197 to 217, wherein the therapeutic factor is a cytokine.

220. The method of clause 156, wherein the cytokine is GM-CSF.

221. The method of any one of clauses 197 to 217, wherein the therapeutic factor is an immune cell growth factor.

222. The method of any one of clauses 197 to 221, wherein the composition further comprises one or more antigens.

223. The method of clause 222, wherein one or more antigens is a protein-based antigen.

224. The method of clause 222, wherein one or more antigens is a peptide-based antigen.

225. The method of any one of clauses 222 to 224, wherein one or more antigens is selected from the group consisting of a cancer antigen, a viral antigen, a bacterial antigen, and a pathogenic antigen.

226. The method of any one of clauses 222 to 224, wherein one or more antigens is a cancer antigen.

227. The method of any one of clauses 222 to 224, wherein one or more antigens is a viral antigen.

228. The method of any one of clauses 222 to 224, wherein one or more antigens is a bacterial antigen.

229. The method of any one of clauses 222 to 224, wherein one or more antigens is a pathogenic antigen.

230. The method of clause 166, wherein the pathogenic antigen is a synthetic or recombinant antigen.

231. The method of any one of clauses 222 to 230, wherein at least one antigen is an HPV protein or peptide.

232. The method of any one of clauses 222 to 231, wherein at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13).

233. The method of any one of clauses 222 to 231, wherein at least one antigen comprises the sequence selected from the group comprising of gp 100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

234. The method of any one of clauses 222 to 231, wherein the antigens comprise one or more of the gp100 sequence (KVPRNQDWL [SEQ. ID. No. 8]) and the TRP2 sequence (SYVDFFVWL [SEQ. ID. No. 9]).

235. The method of any one of clauses 222 to 231, wherein the antigen comprises the sequence RAHYNIVTF (SEQ. ID. NO: 1).

236. The method of any one of clauses 222 to 231, wherein the antigen comprises the sequence GQAEPDRAHYNIVTF (SEQ. ID. NO: 2).

237. The method of any one of clauses 222 to 231, wherein the antigen comprises the sequence KSSGQAEPDRAHYNIVTF (SEQ. ID. NO: 3).

238. The method of any one of clauses 222 to 231, wherein the antigen comprises the sequence YMLDLQPETT (SEQ. ID. NO: 4).

239. The method of any one of clauses 222 to 231, wherein the antigen comprises the sequence KSSYMLDLQPETT (SEQ. ID. NO: 5).

240. The method of any one of clauses 222 to 231, wherein the antigen comprises the sequence MHGDTPTLHEYMLDLQPETT (SEQ. ID. NO: 6).

241. The method of any one of clauses 222 to 231, wherein the antigen comprises the sequence LLMGTLGIVCPICSQKP (SEQ. ID. NO: 7).

242. The method of any one of clauses 222 to 231, wherein the antigen comprises the sequence KVPRNQDWL (SEQ. ID. NO: 8).

243. The method of any one of clauses 222 to 231, wherein the antigen comprises the sequence SYVDFFVWL (SEQ. ID. NO: 9).

244. The method of any one of clauses 222 to 231, wherein the antigen comprises the sequence KYICNSSCM (SEQ. ID. NO: 10).

245. The method of any one of clauses 222 to 231, wherein the antigen comprises the sequence KSSKVPRNQDWL (SEQ. ID. NO: 11).

246. The method of any one of clauses 222 to 231, wherein at least one antigen is selected from the group consisting of a lipoprotein, a lipopeptide, and a protein or peptide modified with an amino acid sequence having an increased hydrophobicity or a decreased hydrophobicity.

247. The method of any one of clauses 222 to 246, wherein one or more antigens is a lipidated antigen or an antigen modified to increase hydrophobicity of the antigen.

248. The method of any one of clauses 222 to 247, wherein at least one antigen is a modified protein or peptide.

249. The method of clause 248, wherein the modified protein or peptide is bonded to a hydrophobic group.

250. The method of clause 248, wherein the modified protein or peptide bonded to a hydrophobic group further comprises a linker sequence between the antigen and the hydrophobic group.

251. The method of clause 249 or 250, wherein the hydrophobic group is a palmitoyl group.

252. The method of any one of clauses 222 to 251, wherein at least one antigen is an unmodified protein or peptide.

253. The method of any one of clauses 197 to 252, wherein the administration activates an immune response via the MAP kinase signaling pathway in cells of the immune system of the mammal.

254. The method of clause 253, wherein the MAP kinase signaling pathway is activated by stimulating at least one of ERK-1, ERK-2, and p38.

255. The method of clause 253 or clause 254, wherein the immune response activates cytotoxic T lymphocytes in the mammal.

256. The method of clause 255, wherein the cytotoxic T lymphocytes are CD8+ T cells.

257. The method of any one of clauses 253 to 256, wherein the immune response activates an antibody response in the mammal.

258. The method of any one of clauses 253 to 257, wherein the immune response activates interferon-gamma (IFN-γ) in the mammal.

259. The method of any one of clauses 197 to 258, wherein the administration enhances functional antigen-specific CD8+ T lymphocyte response.

260. The vaccine composition of any one of clauses 24 to 34 or clauses 48 to 58, wherein the antigen comprises the sequence KSSMHGDTPTLHEYMLDLQPETT (SEQ. ID. NO: 12).

261. The vaccine composition of any one of clauses 24 to 34 or clauses 48 to 58, wherein the antigen comprises the sequence KSSLLMGTLGIVCPICSQKP (SEQ. ID. NO: 13).

262. The method of any one of clauses 91 to 100 or clauses 115 to 128, wherein the antigen comprises the sequence KSSMHGDTPTLHEYMLDLQPETT (SEQ. ID. NO: 12).

263. The method of any one of clauses 91 to 100 or clauses 115 to 128, wherein the antigen comprises the sequence KSSLLMGTLGIVCPICSQKP (SEQ. ID. NO: 13).

264. The method of any one of clauses 159 to 168 or clauses 183 to 196, wherein the antigen comprises the sequence KSSMHGDTPTLHEYMLDLQPETT (SEQ. ID. NO: 12).

265. The method of any one of clauses 159 to 168 or clauses 183 to 196, wherein the antigen comprises the sequence KSSLLMGTLGIVCPICSQKP (SEQ. ID. NO: 13).

266. The method of any one of clauses 222 to 231 or clauses 246 to 259, wherein the antigen comprises the sequence KSSMHGDTPTLHEYMLDLQPETT (SEQ. ID. NO: 12).

267. The method of any one of clauses 222 to 231 or clauses 246 to 259, wherein the antigen comprises the sequence KSSLLMGTLGIVCPICSQKP (SEQ. ID. NO: 13).

Figure 1:
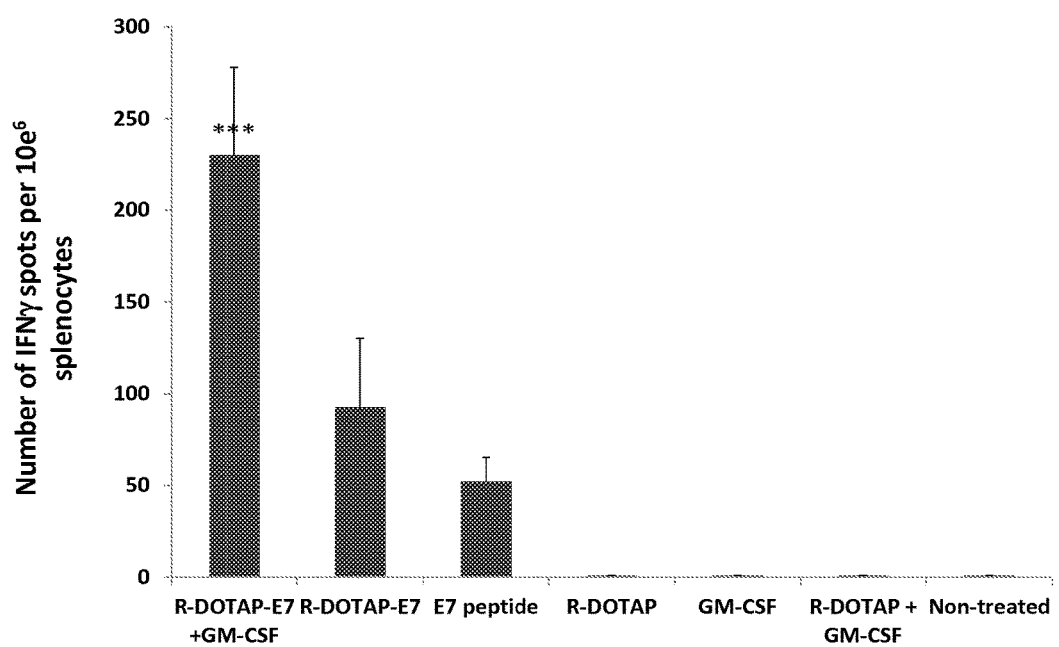
FIG. 1 shows the effect of various vaccine compositions on the antigen-specific immune response in tumor-bearing mice. The number of IFN-ã spots observed per $10^6$ splenocytes from mice are presented as number of spots from $E7_{49-57}$ re-stimulated culture minus control antigen re-stimulated culture per million splenocytes±SD. E7 peptide in the figure refers to GM-CSF-E7+Cd40+IFA. (***$P<0.001$).

Various embodiments of the invention are described herein as follows. In one embodiment described herein, a vaccine composition is provided. The vaccine composition comprises an adjuvant and a therapeutic factor.

In another embodiment, a method of reducing an immune suppressor cell population in a mammal is provided. The method comprises the step of administering an effective amount of a vaccine composition to the mammal, wherein the vaccine composition comprises an adjuvant and a therapeutic factor.

In yet another embodiment, a method of augmenting an immune response in a mammal is provided. The method comprises the step of administering an effective amount of a vaccine composition to the mammal, wherein the vaccine composition comprises an adjuvant and a therapeutic factor.

In yet another embodiment, a method of treating a disease in a mammal is provided. The method comprises the step of administering an effective amount of a vaccine composition to the mammal, wherein the vaccine composition comprises an adjuvant and a therapeutic factor.

In the various embodiments, the vaccine composition comprises an adjuvant and a therapeutic factor. As used herein, the term "adjuvant" refers to a substance that enhances, augments and/or potentiates a mammal's immune response to an antigen. As used herein, the term "therapeutic factor" refers to any agent associated with the treatment of disease by inducing, enhancing, or suppressing an immune response. As used herein, a therapeutic factor includes but is not limited to an immune system stimulant, a cell killing agent, a tumor penetration enhancer, a chemotherapeutic agent, or a cytotoxic immune cell. It is contemplated that the vaccine composition includes formulations in which the adjuvant and the therapeutic factor are administered together, as well as formulations in which the adjuvant and the therapeutic factor are administered separately. Doses of the adjuvant and the therapeutic factor are known to those of ordinary skill in the art.

In some embodiments described herein, the adjuvant is an immunomodulator. As used herein, the term "immunomodulator" refers to an immunologic modifier that enhances, directs, and/or promotes an immune response in a mammal.

In some embodiments described herein, the adjuvant is a nanoparticle. As used herein, the term "nanoparticle" refers to a particle having a size measured on the nanometer scale. As used herein, the "nanoparticle" refers to a particle having a structure with a size of less than about 1,000 nanometers. In some embodiments, the nanoparticle is a liposome.

In some embodiments described herein, the adjuvant is a cationic lipid. As used herein, the term "cationic lipid" refers to any of a number of lipid species which carry a net positive charge at physiological pH or have a protonatable group and are positively charged at pH lower than the pKa.

Suitable cationic lipid according to the present disclosure include, but are not limited to: 3-.beta.[.sup.4N-(.sup.1N, .sup.8-diguanidino spermidine)-carbamoyl]cholesterol (BGSC); 3-.beta.[N,N-diguanidinoethyl-aminoethane)-carbamoyl]cholesterol (BGTC); N,N.sup.1N.sup.2N.sup.3Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2(sperminecarboxamido)ethyl]-N,N-dimethyl-1-p-ropanaminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N-tetramethyl-N,N-bis(2-hydroxyethyl)-2,3-dioleoyloxy-1,4-butane-diammonium iodide) (Tfx-50); N-1-(2,3-dioleoyloxy) propyl-N,N,N-trimethyl ammonium chloride (DOTMA) or other N-(N,N-1-dialkoxy)-alkyl-N,N,N-trisubstituted ammonium surfactants; 1,2 dioleoyl-3-(4'-trimethylammonio)butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-.beta.-hydroxyethylammonium) or DORIE (DL-1,2-O-dioleoyl-3-dimethylaminopropyl-.beta.-hydroxyethylammoniu-m) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES), cholesteryl-3.beta.-carboxyl-amido-ethylenetrimethylammonium iodide, 1-dimethylamino-3-trimethylammonio-DL-2-propyl-cholesteryl carboxylate iodide, cholesteryl-3-O-carboxyamidoethyleneamine, cholesteryl-3-.beta.-oxysuccinamido-ethylenetrimethylammonium iodide, 1-dimethylamino-3-trimethylammonio-DL-2-propyl-cholesteryl-3-.beta.-oxysu-ccinate iodide, 2-(2-trimethylammonio)-ethylmethylamino ethyl-cholesteryl-3-.beta.-oxysuccinate iodide, 3-.beta.-N-(N',N'-dimethylaminoethane) carbamoyl cholesterol (DC-chol), and 3-.beta.-N-(polyethyleneimine)-carbamoylcholesterol; O,O'-dimyristyl-N-lysyl aspartate (DMKE); O,O'-dimyristyl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-dipalmitoyl-sn-glycero-3-ethylphosphocholine (DPEPC); 1,2-distearoyl-sn-glycero-3-ethylphosphocholine (DSEPC); 1,2-dioleoyl-3-trimethylammonium propane (DOTAP); dioleoyl dimethylaminopropane (DODAP); 1,2-palmitoyl-3-trimethylammonium propane (DPTAP); 1,2- distearoyl-3-trimethylammonium propane (DSTAP), 1,2-myristoyl-3-trimethylammonium propane (DMTAP); and sodium dodecyl sulfate (SDS). Furthermore, structural variants and derivatives of the any of the described cationic lipids are also contemplated.

In some embodiment, the cationic lipid is selected from the group consisting of DOTAP, DOTMA, DOEPC, and combinations thereof. In other embodiments, the cationic lipid is DOTAP. In yet other embodiments, the cationic lipid is DOTMA. In other embodiments, the cationic lipid is DOEPC. In some embodiments, the cationic lipid is purified.

In some embodiments, the cationic lipid is an enantiomer of a cationic lipid. The term "enantiomer" refers to a stereoisomer of a cationic lipid which is a non-superimposable mirror image of its counterpart stereoisomer, for example R and S enantiomers. In various examples, the enantiomer is R-DOTAP or S-DOTAP. In one example, the enantiomer is R-DOTAP. In another example, the enantiomer is S-DOTAP. In some embodiments, the enantiomer is purified. In various examples, the enantiomer is R-DOTMA or S-DOTMA. In one example, the enantiomer is R-DOTMA. In another example, the enantiomer is S-DOTMA. In some embodiments, the enantiomer is purified. In various examples, the enantiomer is R-DOPEC or S-DOPEC. In one example, the enantiomer is R-DOPEC. In another example, the enantiomer is S-DOPEC. In some embodiments, the enantiomer is purified.

In various embodiments described herein, the therapeutic factor is selected from the group consisting of interleukins 1-18, stem cell factor, basic FGF, EGF, G-CSF, GM-CSF, FLK-2 ligand, HILDA, MIP-1α, TGF-β, TGF-α, M-CSF, IFN-γ, IFN-α, IFN-β, soluble CD23, LT, and combinations thereof. Other therapeutic factors are known to those of ordinary skill in the art and may also be used in the vaccine compositions of the present disclosure.

In various embodiments described herein, the therapeutic factor is a cytokine. In some embodiments, the cytokine is GM-CSF. In other embodiments described herein, the therapeutic factor is an immune cell growth factor.

In various embodiments described herein, the composition further comprises one or more antigens. As used herein, the term "antigen" refers to any agent (e.g., protein, peptide, polysaccharide, glycoprotein, glycolipid, nucleic acid, or combination thereof) that, when introduced into a mammal having an immune system (directly or upon expression as in, e.g., DNA vaccines), is recognized by the immune system of the mammal and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR).

In some embodiments, one or more antigens is a protein-based antigen. In other embodiments, one or more antigens is a peptide-based antigen. In various embodiments, one or more antigens is selected from the group consisting of a cancer antigen, a viral antigen, a bacterial antigen, and a pathogenic antigen. A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In one embodiment, the antigen is a cancer antigen. In one embodiment, the antigen is a viral antigen. In another embodiment, the antigen is a bacterial antigen. In various embodiments, the antigen is a pathogenic antigen. In some embodiments, the pathogenic antigen is a synthetic or recombinant antigen.

In some embodiments, the antigen is a cancer antigen. A "cancer antigen," as used herein, is a molecule or compound (e.g., a protein, peptide, polypeptide, lipoprotein, lipopeptide, glycoprotein, glycopeptides, lipid, glycolipid, carbohydrate, RNA, and/or DNA) associated with a tumor or cancer cell and which is capable of provoking an immune response (humoral and/or cellular) when expressed on the surface of an antigen presenting cell in the context of an MHC molecule. For example, a cancer antigen may be a tumor-associated antigen. Tumor-associated antigens include self antigens, as well as other antigens that may not be specifically associated with a cancer, but nonetheless enhance an immune response to and/or reduce the growth of a tumor or cancer cell when administered to a mammal. In one embodiment, at least one antigen is an HPV protein or peptide.

In some embodiments of the present disclosure, at least one antigen comprises a sequence selected from the group consisting of RAHYNIVTF (SEQ. ID. NO: 1), GQAEPDRAHYNIVTF (SEQ. ID. NO: 2), KSSGQAEPDRAHYNIVTF (SEQ. ID. NO: 3), YMLDLQPETT (SEQ. ID. NO: 4), KSSYMLDLQPETT (SEQ. ID. NO: 5), MHGDTPTLHEYMLDLQPETT (SEQ. ID. NO: 6), LLMGTLGIVCPICSQKP (SEQ. ID. NO: 7), KVPRNQDWL (SEQ. ID. NO: 8), SYVDFFVWL (SEQ. ID. NO: 9), KYICNSSCM (SEQ. ID. NO: 10), KSSKVPRNQDWL (SEQ. ID. NO: 11), KSSMHGDTPTLHEYMLDLQPETT (SEQ. ID. NO: 12), and KSSLLMGTLGIVCPICSQKP (SEQ. ID. NO: 13). In one embodiment, at least one antigen comprises the sequence RAHYNIVTF (SEQ. ID. NO: 1). In another embodiment, at least one antigen comprises the sequence GQAEPDRAHYNIVTF (SEQ. ID. NO: 2). In yet another embodiment, at least one antigen comprises the sequence KSSGQAEPDRAHYNIVTF (SEQ. ID. NO: 3). In some embodiments, KSSGQAEPDRAHYNIVTF (SEQ. ID. NO: 3) is modified to further comprise a hydrophobic group. In one embodiment, the hydrophobic group is a palmitoyl group.

In other embodiments, at least one antigen comprises the sequence YMLDLQPETT (SEQ. ID. NO: 4). In another embodiment, at least one antigen comprises the sequence KSSYMLDLQPETT (SEQ. ID. NO: 5). In yet another embodiment, KSSYMLDLQPETT (SEQ. ID. NO: 5) is modified to further comprise a hydrophobic group. In one embodiment, the hydrophobic group is a palmitoyl group.

In other embodiments, at least one antigen comprises the sequence MHGDTPTLHEYMLDLQPETT (SEQ. ID. NO: 6). In another embodiment, MHGDTPTLHEYMLDLQPETT (SEQ. ID. NO: 6) is modified to further comprise a hydrophobic group. In one embodiment, the hydrophobic group is a palmitoyl group.

In other embodiments, at least one antigen comprises the sequence LLMGTLGIVCPICSQKP (SEQ. ID. NO: 7). In some embodiments, LLMGTLGIVCPICSQKP (SEQ. ID. NO: 7) is modified to further comprise a hydrophobic group. In one embodiment, the hydrophobic group is a palmitoyl group.

In some embodiments, at least one antigen comprises the sequence KVPRNQDWL (SEQ. ID. NO: 8). In other embodiments, at least one antigen comprises the sequence SYVDFFVWL (SEQ. ID. NO: 9). In yet other embodiments, at least one antigen comprises the sequence KYICNSSCM (SEQ. ID. NO: 10). In another embodiment, at least one antigen comprises the sequence KSSKVPRNQDWL (SEQ. ID. NO: 11). In some embodiments, KSSKVPRNQDWL (SEQ. ID. NO: 11) is modified to further comprise a hydrophobic group. In one embodiment, the hydrophobic group is a palmitoyl group.

In other embodiments, at least one antigen comprises the sequence KSSMHGDTPTLHEYMLDLQPETT (SEQ. ID. NO: 12). In another embodiment, KSSMHGDTPTLHEYMLDLQPETT (SEQ. ID. NO: 12) is modified to further comprise a hydrophobic group. In one embodiment, the hydrophobic group is a palmitoyl group.

In other embodiments, at least one antigen comprises the sequence KSSLLMGTLGIVCPICSQKP (SEQ. ID. NO: 13). In some embodiments, KSSLLMGTLGIVCPICSQKP (SEQ. ID. NO: 13) is modified to further comprise a hydrophobic group. In one embodiment, the hydrophobic group is a palmitoyl group.

In one embodiment, the antigen comprises the sequence selected from the group comprising of gp100 (KVPRNQDWL [SEQ. ID. No. 8]), TRP2 (SYVDFFVWL [SEQ. ID. No. 9]), and p53 (KYICNSSCM [SEQ. ID. No. 10]), and combinations thereof.

In one embodiment, the antigens comprise one or more of the gp100 sequence (KVPRNQDWL [SEQ. ID. No. 8]) and the TRP2 sequence (SYVDFFVWL [SEQ. ID. No. 9]).

In various embodiments, at least one antigen is selected from the group consisting of a lipoprotein, a lipopeptide, and a protein or peptide modified with an amino acid sequence having an increased hydrophobicity or a decreased hydrophobicity. In some embodiments, one or more antigens is an antigen modified to increase hydrophobicity of the antigen. In one embodiment, at least one antigen is a modified protein or peptide. In some embodiments, the modified protein or peptide is bonded to a hydrophobic group. In other embodiments, the modified protein or peptide bonded to a hydrophobic group further comprises a linker sequence between the antigen and the hydrophobic group. In some embodiments, the hydrophobic group is a palmitoyl group. In yet other embodiments, at least one antigen is an unmodified protein or peptide.

In various embodiments described herein, the vaccine composition induces an immune response in a mammal by activating the mitogen-activated protein (MAP) kinase signaling pathway. Induction of an immune response by adjuvants such as cationic lipids are described, for example, in PCT/US2008/057678 (WO/2008/116078; "Stimulation of an Immune Response by Cationic Lipids") and PCT/US2009/040500 (WO/2009/129227; "Stimulation of an Immune Response by Enantiomers of Cationic Lipids"), the entire disclosures of both incorporated herein by reference. In some embodiments, the MAP kinase signaling pathway is activated by stimulating at least one of extracellular signal-regulated kinase ("ERK")-1, ERK-2, and p38. In other embodiments, the composition enhances functional antigen-specific CD8+ T lymphocyte response. The term "mammal" is well known to those of skill in the art. In one embodiment, the mammal is a human.

In one embodiment described herein, a method of reducing an immune suppressor cell population in a mammal is provided. The method comprises comprising the step of administering an effective amount of a vaccine composition to the mammal, wherein the vaccine composition comprises an adjuvant and a therapeutic factor. The previously described embodiments of the vaccine composition are applicable to the method of reducing an immune suppressor cell population in a mammal described herein.

In some embodiments, the immune suppressor cell is a myeloid-derived suppressor cell (MDSC). In other embodiments, the immune suppressor cell is a T regulatory cell.

In various embodiments, the reduction results in an increase in T-cell response in the mammal. In some embodiments, the T-cell is a tumor-infiltrated T-cell. In some embodiments, the T-cell response is a CD4+ T-cell response. In certain embodiments, the CD4+ T-cell is a tumor-infiltrated CD4+ T-cell. In some embodiments, the T-cell response is a CD8+ T-cell response. In certain embodiments, the CD8+ T-cell is a tumor-infiltrated CD8+ T-cell.

In various embodiments, the mammal is a human. In some embodiments, the administration activates an immune response via the MAP kinase signaling pathway in cells of the immune system of the mammal. In various embodiments, the MAP kinase signaling pathway is activated by stimulating at least one of ERK-1, ERK-2, and p38.

In other embodiments, the immune response activates cytotoxic T lymphocytes in the mammal. In one embodiment, the cytotoxic T lymphocytes are CD8+ T cells. In another embodiment, the administration enhances functional antigen-specific CD8+ T lymphocyte response. In yet another embodiment, the immune response activates an antibody response in the mammal. In other embodiments, the immune response activates interferon-gamma (IFN-ã) in the mammal.

In one embodiment described herein, a method of augmenting an immune response in a mammal is provided. The method comprises the step of administering an effective amount of a vaccine composition to the mammal, wherein the vaccine composition comprises an adjuvant and a therapeutic factor. The previously described embodiments of the vaccine composition and of the method of reducing an immune suppressor cell population in a mammal are applicable to the method of augmenting an immune response in a mammal described herein.

In one embodiment described herein, a method of treating a disease in a mammal is provided. The method comprises the step of administering an effective amount of a vaccine composition to the mammal, wherein the vaccine composition comprises an adjuvant and a therapeutic factor. The previously described embodiments of the vaccine composition and of the method of reducing an immune suppressor cell population in a mammal are applicable to the method of treating a disease in a mammal described herein.

In some embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse. In one embodiment, the method is a prophylactic treatment. In some embodiments, the disease is a cancer.

EXAMPLE 1

Preparation of Adjuvant and Adjuvants Incorporating an Antigen

Adjuvants may be prepared using cationic lipids alone. Alternatively, adjuvants may be prepared using mixtures of cationic lipids and other immunomodulators. Vaccine compositions may be prepared using a cationic lipid-based composition incorporating an antigen. In the present example, DOTAP was used as an exemplary cationic lipid and HPV protein E7 peptide antigen was used as an exemplary antigen.

Sterile water for injection (WFI) or a buffer was used in all procedures in which cationic lipids were prepared into liposomes. In this example, liposomes were prepared using lipid films. The E7 antigen used for incorporation into the liposomes was an H-2D$^b$ restricted CTL epitope (amino acid 49-57, RAHYNIVTF [SEQ. ID. NO. 1]) derived from HPV 16 E7 protein. Lipid films were made in glass vials by (1) dissolving the lipids in an organic solvent such as chloroform, and (2) evaporating the chloroform solution under a steady stream of dry nitrogen gas. Traces of organic solvent were removed by keeping the films under vacuum overnight. The lipid films were then hydrated by adding the required amount of WFI or buffer to make a final concentration of 4-10 mg/mL. The suspensions were then extruded to a size of 200 nm and stored at 4° C.

For the preparation of cationic lipid incorporating an antigen, the DOTAP lipid film was rehydrated by an aqueous solution of E7 peptide. Other methods used in general liposome preparation that are well known to those skilled in the art may also be used.

EXAMPLE 2

Effect of Vaccine Compositions on Antigen-Specific Immune Response in Tumor-Bearing Mice Various vaccine compositions may be compared according to the present disclosure and evaluated for their effects on antigen-specific immune response in tumor-bearing mice. In this example, R-DOTAP was used as an exemplary cationic lipid, E7 peptide was used as an exemplary antigen, and the cytokine GM-CSF was used as an exemplary therapeutic factor. Furthermore, anti-CD40 Ab and incomplete Freund's adjuvant (IFA) were used as comparative adjuvants.

In this example, vaccine compositions were prepared according to the disclosure and the following groups were evaluated:
Group 1: R-DOTAP-E7 peptide (20 µg/mouse) and GM-CSF (5 µg/mouse)
Group 2: R-DOTAP-E7 peptide (20 µg/mouse)
Group 3: GM-CSF (5 µg/mouse), E7 peptide (100 ug/mouse), anti-CD40 Ab (20 µg/mouse), and IFA (50 µg/mouse)
Group 4: R-DOTAP alone
Group 5: GM-CSF alone
Group 6: R-DOTAP and GM-CSF
Group 7: Untreated control Female C57BL6 mice aged 6-8 weeks old (5 mice per group) were implanted with 50,000 TC-1 cells/mouse subcutaneously in the right flank on day 0. On day 8, when all mice had tumors of ~3-4 mm in diameter, subjects from each group were with the vaccine composition of the appropriate group.

Treatment was repeated on day 15. Six days later (i.e., day 21 after tumor implantation), mice were sacrificed. The spleens of the mice were harvested and processed for total lymphocytes. IFNγ activity in the presence of E7$_{49-57}$ peptide vs. irrelevant peptide control (10 µg/ml each) was assayed by ELISPOT. The number of spots from E7$_{49-57}$ re-stimulated culture minus irrelevant antigen re-stimulated culture per million splenocytes was evaluated.

As shown in FIG. 1, Group 1 (i.e., R-DOTAP-E7 peptide and GM-CSF) exhibited a statistically significant increase in antigen-specific immune response in tumor bearing mice compared to the other groups. The combination of R-DOTAP-E7 peptide and GM-CSF exhibited a synergistic effect on antigen-specific immune response compared to the individual components. Group 3 (i.e., GM-CSF, E7 peptide, anti-CD40 Ab, and IFA) was administered growth factor and a non-cationic lipid adjuvant, but did not exhibit a synergistic effect on the immune response as observed with Group 1.

EXAMPLE 3

Effect of Vaccine Compositions on MDSC in the Tumor Micro-Environment of Tumor-Bearing Mice Various vaccine compositions may be compared according to the present disclosure and evaluated for their effects on MDSC number in the tumor micro-environment in tumor-bearing mice. In this example, R-DOTAP was used as an exemplary cationic lipid, E7 peptide was used as an exemplary antigen, and the cytokine GM-CSF was used as an exemplary therapeutic factor.

In this example, vaccine compositions were prepared according to the disclosure and the following groups were evaluated:
Group 1: R-DOTAP-E7 peptide (20 µg/mouse) and GM-CSF (5 µg/mouse)
Group 2: R-DOTAP-E7 peptide (20 µg/mouse)
Group 3: R-DOTAP alone
Group 4: GM-CSF alone
Group 5: R-DOTAP and GM-CSF
Group 6: Untreated control Female C57BL6 mice aged 6-8 weeks old (5 mice per group) were implanted with 50,000 TC-1 cells/mouse subcutaneously in the right flank on day 0. On day 8, when all mice had tumors of ~3-4 mm in diameter, subjects from each group were with the vaccine composition of the appropriate group.

Treatment was repeated on day 15. Six days later (i.e., day 21 after tumor implantation), tumor tissue was harvested from the mice. Tumor samples were processed using GentleMACS Dissociator (Miltenyi Biotec, Auburn, Calif.) and the solid tumor homogenization protocol, as suggested by the manufacturer.

The number of tumor-infiltrated MDSC (defined as CD11b$^+$Gr-1$^+$ cells) was analyzed within the population of CD44$^+$ cells (marker for hematopoietic cells) using flow cytometry assay. The numbers of tumor-infiltrated cells were standardized per 1×106 of total tumor cells and presented as mean values.

Figure 2:
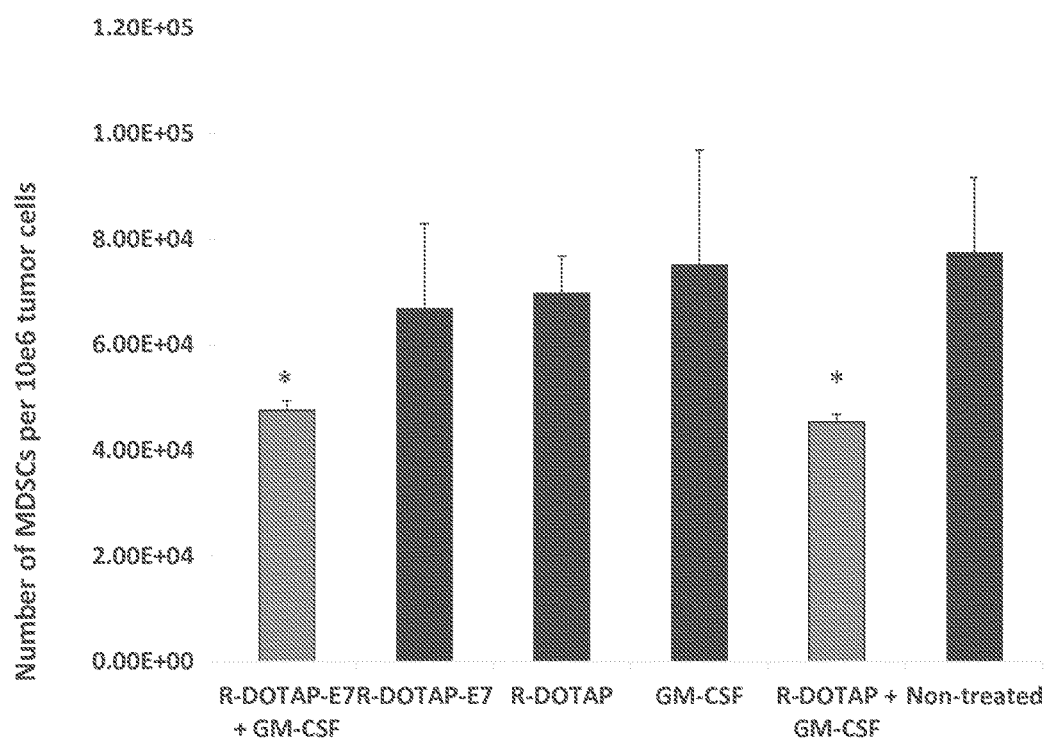
FIG. 2 shows the effect of various vaccine compositions on the number of tumor-infiltrated MDSC (defined as $CD11b^+Gr-1^+$ cells within the population of $CD44^+$ cells) using a flow cytometry assay. The numbers of tumor-infiltrated cells are standardized per $1\times10^6$ of total tumor cells and presented as mean values±SD. (*$P<0.05$ compared to the untreated and GM-CSF only groups).

As shown in FIG. 2, both Group 1 (i.e., R-DOTAP-E7 peptide and GM-CSF) and Group 5 (i.e., R-DOTAP-E7 and GM-CSF) exhibited a statistically significant decrease in MDSC number in tumor bearing mice compared to untreated mice and mice treated with GM-CSF only. The combination of R-DOTAP-E7 peptide and GM-CSF exhibited a synergistic effect to reduce the number of MDSC compared to the individual components. In addition, the combination of R-DOTAP and GM-CSF (i.e., without the administration of an antigen) exhibited a similar synergistic effect to reduce the number of MDSC compared to the individual components.

EXAMPLE 4

Effect of Vaccine Compositions on Tumor-Infiltrating CD8+ T-cells in Tumor-Bearing Mice Various vaccine compositions may be compared according to the present disclosure and evaluated for their effects on the number of tumor-infiltrating CD8+ T-cells in tumor-bearing mice. In this example, R-DOTAP was used as an exemplary cationic lipid, E7 peptide was used as an exemplary antigen, and the cytokine GM-CSF was used as an exemplary therapeutic factor.

In this example, vaccine compositions were prepared according to the disclosure and the following groups were evaluated:

Group 1: R-DOTAP-E7 peptide (20 µg/mouse) and GM-CSF (5 µg/mouse)

Group 2: R-DOTAP-E7 peptide (20 µg/mouse)

Group 3: R-DOTAP alone

Group 4: GM-CSF alone

Group 5: R-DOTAP and GM-CSF

Group 6: Untreated control

Female C57BL6 mice aged 6-8 weeks old (5 mice per group) were implanted with 50,000 TC-1 cells/mouse subcutaneously in the right flank on day 0. On day 8, when all mice had tumors of ~3-4 mm in diameter, subjects from each group were with the vaccine composition of the appropriate group.

Treatment was repeated on day 15. Six days later (i.e., day 21 after tumor implantation), tumor tissue was harvested from the mice. Tumor samples were processed using GentleMACS Dissociator (Miltenyi Biotec, Auburn, Calif.) and the solid tumor homogenization protocol, as suggested by the manufacturer.

The number of tumor-infiltrated CD8+ T-Cells were analyzed within the population of $CD44^+$ cells (marker for hematopoietic cells) using flow cytometry assay. The numbers of tumor-infiltrated cells were standardized per $1\times10^6$ of total tumor cells and presented as mean values.

Figure 3:
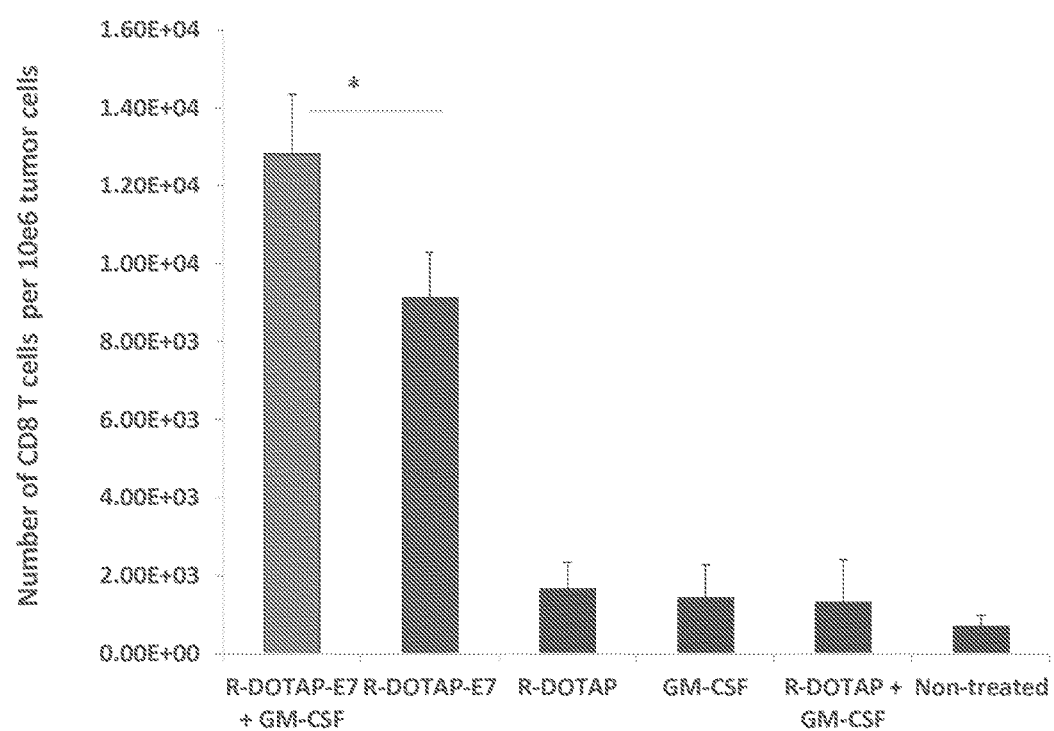
FIG. 3 shows the effect of various vaccine compositions on the number of tumor-infiltrating CD8+ T-cells following administration to mice. The number of tumor-infiltrated CD8+ T-Cells was analyzed within the population of $CD44^+$ cells using flow cytometry assay. The numbers of tumor-infiltrated cells were standardized per 1×106 of total tumor cells and are presented as mean values±SD. (*$P<0.05$).

As shown in FIG. 3, both Group 1 (i.e., R-DOTAP-E7 peptide and GM-CSF) and Group 2 (i.e., R-DOTAP-E7) exhibited a statistically significant increase in the number of tumor-infiltrated CD8+ T-Cells in tumor bearing mice compared to the other groups. The combination of R-DOTAP-E7 peptide and GM-CSF exhibited a synergistic effect to increase the number of tumor-infiltrated CD8+ T-Cells compared to the individual components.

EXAMPLE 5

Effect of Vaccine Compositions on Antigen-Specific Immune Response in Mice

Various vaccine compositions may be compared according to the present disclosure and evaluated for their effects on antigen-specific immune response in mice. In this example, R-DOTAP was used as an exemplary cationic lipid, TRP-2 and gp100 peptides were used as an exemplary antigen, and the cytokine GM-CSF was used as an exemplary therapeutic factor.

In this example, vaccine compositions were prepared according to the disclosure and the following groups were evaluated:

Group 1: R-DOTAP/TRP-2/gp100 peptide (190 ug/160 ug)

Group 2: R-DOTAP/TRP-2/gp 100 peptide/GM-CSF (190 ug/160 ug/0.5 ug)

Female C57BL6 mice aged 6-8 weeks old (4 mice per group) were used in the study. On days 0 and 8, subjects from each group were with the vaccine composition of the appropriate group.

Seven days later (i.e., day 14 after first administration), mice were sacrificed and their spleens were harvested and processed for total lymphocytes. IFNγ activity in the presence of TRP-2 and gp-100 peptides vs. irrelevant peptide control (10 µg/ml each) was assayed by ELISPOT. Values were presented as number of spots from TRP-2 and gp100 re-stimulated culture minus irrelevant antigen re-stimulated culture per million splenocytes.

Figure 4:
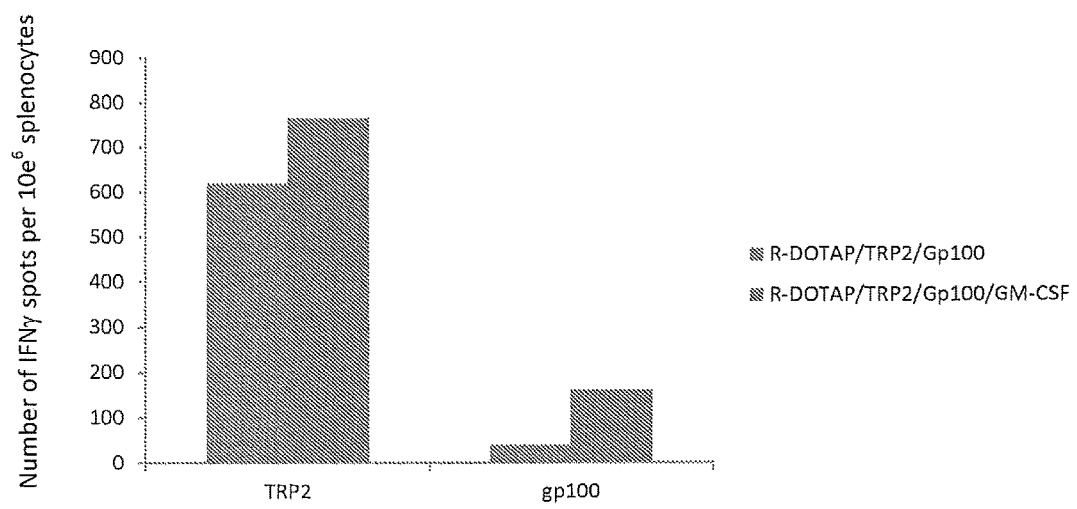
FIG. 4 shows the effect of various vaccine compositions on antigen-specific immune response. IFNγ activity in the presence of the melanoma antigens TRP-2 and gp-100 peptides vs. peptide control (10 μg/ml each) was assayed by ELISPOT. Values are presented as number of spots from TRP-2 and gp100 re-stimulated culture minus control antigen re-stimulated culture per million splenocytes. (*$P<0.01$).

As shown in FIG. 4, Group 2 (i.e., R-DOTAP/TRP-2/gp100 peptide/GM-CSF) exhibited a statistically significant increase in antigen-specific immune response compared to Group 1, which did not include GM-CSF.

While the invention has been illustrated and described in detail in the foregoing description, such an illustration and description is to be considered as exemplary and not restrictive in character, it being understood that only the illustrative embodiments have been described and that all changes and modifications that come within the scope of the invention are desired to be protected. Those of ordinary skill in the art may readily devise their own implementations that incorporate one or more of the features described herein, and thus fall within the scope of the present disclosure.

What is claimed is:

1. A composition consisting essentially of a cationic lipid and GM-CSF, wherein the cationic lipid consists of DOTAP, wherein the composition is in a dosage sufficient to reduce a myeloid-derived suppressor cell population in a tumor microenvironment of a subject.

2. The composition of claim 1, wherein the cationic lipid is an enantiomer of the cationic lipid.

3. The composition of claim 2, wherein the enantiomer is R-DOTAP.

* * * * *